United States Patent
Atia et al.

(10) Patent No.: US 8,059,277 B2
(45) Date of Patent: Nov. 15, 2011

(54) MODE HOPPING SWEPT FREQUENCY LASER FOR FD OCT AND METHOD OF OPERATION

(75) Inventors: Walid A. Atia, Lexington, MA (US); Mark E. Kuznetsov, Lexington, MA (US); Dale C. Flanders, Lexington, MA (US)

(73) Assignee: Axsun Technologies, Inc., Billerica, MA (US)

( * ) Notice: Subject to any disclaimer, the term of this patent is extended or adjusted under 35 U.S.C. 154(b) by 952 days.

(21) Appl. No.: 12/027,709

(22) Filed: Feb. 7, 2008

(65) Prior Publication Data
US 2009/0059970 A1 Mar. 5, 2009

Related U.S. Application Data

(60) Provisional application No. 60/968,185, filed on Aug. 27, 2007.

(51) Int. Cl.
*G01B 9/02* (2006.01)
*G01B 11/02* (2006.01)
(52) U.S. Cl. ......................... 356/479; 356/497
(58) Field of Classification Search .................. 356/479, 356/497
See application file for complete search history.

(56) References Cited

U.S. PATENT DOCUMENTS

| | | | |
|---|---|---|---|
| 6,160,826 A * | 12/2000 | Swanson et al. | 372/20 |
| 6,611,546 B1 | 8/2003 | Garnache et al. | |
| 2002/0074485 A1 | 6/2002 | Atia et al. | |
| 2005/0008045 A1 | 1/2005 | Xie et al. | |
| 2006/0203859 A1 * | 9/2006 | Cable et al. | 372/20 |
| 2006/0215713 A1 | 9/2006 | Flanders et al. | |
| 2007/0002327 A1 | 1/2007 | Zhou et al. | |

FOREIGN PATENT DOCUMENTS

JP 11-307879 A 11/1999

OTHER PUBLICATIONS

Wei et al. "A Fiber Based Interferometer with Discrete Tunable Laser for Fourier Domain Optical Coherence Tomography" Biophotonics, Nanophotonics and Metamaterials, International Symposium on Metamaterials, pp. 64-67, Oct. 16-18, 2006.*
Wei, Luo, et al, "A Fiber Based Interferometer with Discrete Tunable Laser for Fourier Domain Optical Coherence Tomography,"Biophotonics, Nanophotonics and Metamaterials, International Symposium on Metamaterials, pp. 64-67, Oct. 16-18, 2006.
Huber, R., et al., "Amplified, Frequency Swept Lasers for Frequency Domain Reflectometry and OCT Imaging: Design and Scaling Principles," Optics Express, vol. 13, No. 9, May 2, 2005, pp. 3513-3528.

* cited by examiner

*Primary Examiner* — Patrick J Connolly
(74) *Attorney, Agent, or Firm* — Houston Eliseeva, LLP

(57) ABSTRACT

A frequency swept laser source that generates an optical signal that is tuned over a spectral scan band at single discrete wavelengths associated with longitudinal modes of the swept laser source. Laser hopping over discrete single cavity modes allows long laser coherence length even under dynamic very high speed tuning conditions. A ramp drive to the laser is used to linearize laser frequency tuning. A beam splitter is used to divide the optical signal between a reference arm leading to a reference reflector and a sample arm leading to a sample. A detector system detects the optical signal from the reference arm and the sample arm for generating depth profiles and images of the sample.

35 Claims, 4 Drawing Sheets

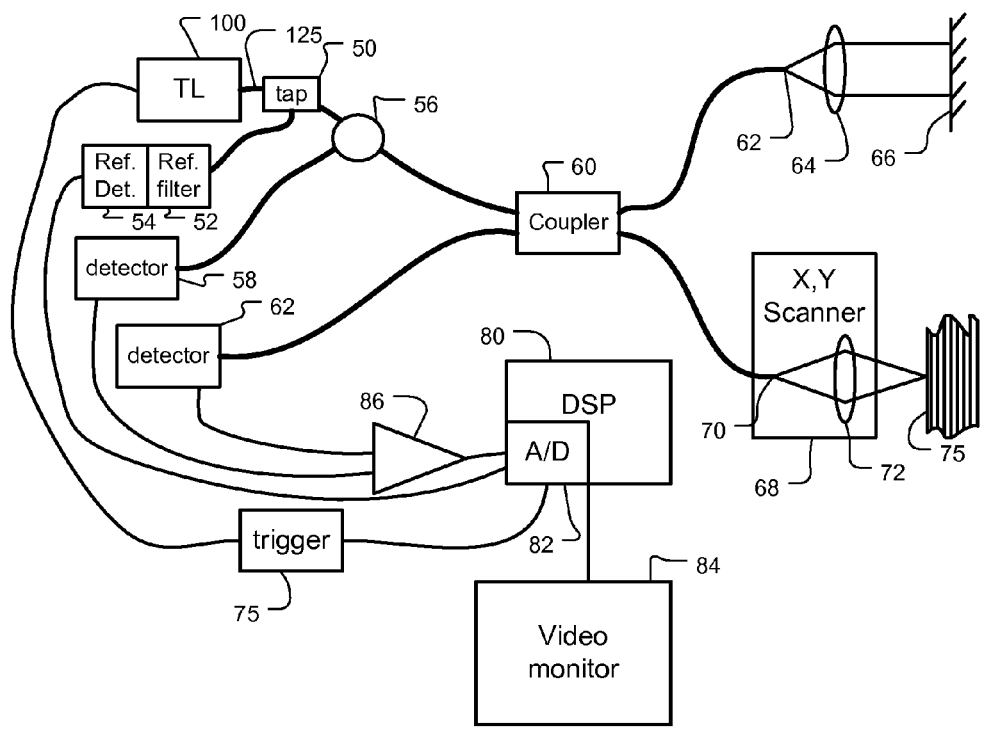
Fig. 1
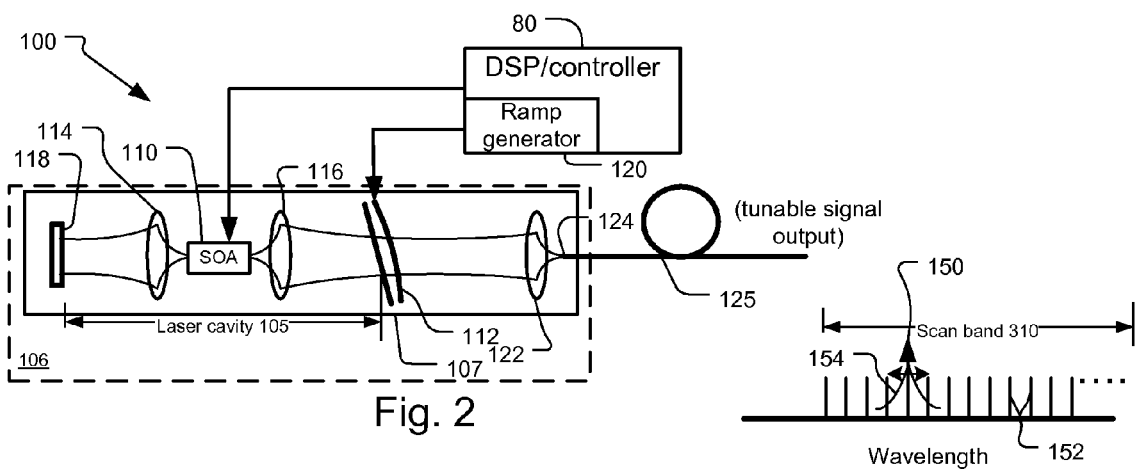
Fig. 2
Fig. 3

MODE HOPPING SWEPT FREQUENCY LASER FOR FD OCT AND METHOD OF OPERATION

RELATED APPLICATIONS

This application claims the benefit under 35 USC 119(e) of U.S. Provisional Application No. 60/968,185, filed on Aug. 27, 2007.

This application is related to U.S. application Ser. No. 12/027,710 filed on Feb. 7, 2008, now U.S. Patent Publication No.: US 2009/0059971 A1, which is incorporated herein by reference in its entirety.

BACKGROUND OF THE INVENTION

Optical coherence analysis relies on the use of the interference phenomena between a reference wave and an experimental wave or between two parts of an experimental wave to measure distances and thicknesses, and calculate indices of refraction of a sample. Optical Coherence Tomography (OCT) is one example technology that is used to perform usually high-resolution cross sectional imaging that can provide images of biological tissue structure, for example, on the microscopic scales in real time. Optical waves are sent through an object and a computer produces images of cross sections of the object by using information on how the waves are changed.

The original OCT imaging technique, the time-domain OCT (TD-OCT) uses a movable reference mirror in a Michelson interferometer arrangement. Another type of optical coherence analysis is termed Fourier domain OCT (FD-OCT). Other terms are time encoded Frequency Domain OCT and swept source OCT. These techniques use either a wavelength swept source and a single detector, sometimes referred to as time-encoded FD-OCT or TEFD-OCT, or a broadband source and spectrally resolving detector system, sometimes referred to spectrum-encoded FD-OCT or SEFD-OCT. FD-OCT has advantages over time domain OCT (TD-OCT) in speed and signal-to-noise ratio (SNR).

TEFD-OCT has advantages over SEFD-OCT in some respects. The spectral components are not encoded by spatial separation, but they are encoded in time. The spectrum is either filtered or generated in successive frequency steps and reconstructed before Fourier-transformation. Using the frequency scanning light source (i.e. wavelength tuned laser) the optical configuration becomes less complex but the critical performance characteristics now reside in the wavelength tuned laser.

SUMMARY OF THE INVENTION

Frequency swept laser source for TEFD-OCT imaging requires tuning at very high repetition rates, in the tens of kilohertz, for fast real-time image frame acquisition with a sufficiently large image pixel count. At the same time, long coherence length of the source is required for large imaging depth range. Simultaneous high speed tuning while maintaining long coherence length is difficult to achieve in conventional tunable lasers, such as conventional external cavity semiconductor tunable lasers.

Long laser coherence length requires narrow spectral linewidth operation and therefore demands a narrow bandwidth tunable filter for the laser. Fast tuning of a narrow filter implies laser light makes very few roundtrips inside the laser cavity as the filter shifts its center frequency by its width. Few roundtrips imply detrimental decrease of coherence length of the laser. We define dwell time as the number of roundtrips light makes inside the laser cavity while intracavity tunable filter tunes by its full width at half maximum. As the laser tuning speed is increased and the dwell time decreases to less than about 2, the laser coherence length degrades very rapidly and eventually the laser power turns off completely. One solution to this problem is the frequency domain modelocked laser (FDML), where light in a kilometer long fiber cavity is repetitively filtered by the tunable filter on multiple round trips in the cavity, such that long coherence length is maintained even at high tuning speeds. Such a laser, however, is bulky, has complications related to using very long fiber, and has a number of other limitations.

Dwell time of a tunable laser at high tuning speed can be increased by using a short laser cavity length with a correspondingly small cavity roundtrip time. Such a short required cavity length, e.g. 10 to 30 millimeters (mm), is typically difficult to achieve with conventional external cavity semiconductor lasers. Using micro-electro-mechanical system (MEMS) tunable filters and optical micro-bench packaging allows such compact tunable lasers, however.

Furthermore, as the cavity length gets smaller, cavity mode spacing gets larger, so that fewer modes remain lasing under the narrow tunable filter spectral envelope, eventually leaving just a single lasing mode. Conventional thinking has assumed that a continuously tuned laser mode or a group of modes is required for OCT imaging. However, since OCT data is read at discrete time intervals anyway, a laser tuned over a discrete set of individual wavelengths should be also suitable for OCT imaging. Such a discretely tuned single mode laser can have a short laser cavity and thus capable of operating at very high speeds with dwell times sufficiently high for maintaining the long required dynamic coherence length.

The present invention concerns a wavelength tuned laser for an optical coherence analysis system. The laser hops between single discrete modes of the laser cavity. The laser can be tuned at very high scanning speeds while maintaining long coherence length. Further, laser frequency tuning with time can be linearized with a high utilization duty cycle.

In general, according to one aspect, the invention features an optical coherence analysis system. This system comprises a swept laser source that generates an optical signal that is tuned over a spectral scan band at discrete wavelengths associated with longitudinal modes of the swept laser source. A beam splitter is used to divide the optical signal between a reference arm leading to a reference reflector and a sample arm leading to a sample. A detector system detects the optical interference signal from the reference arm and the sample arm.

In the preferred embodiment, the swept laser source comprises: a laser cavity defining the longitudinal modes, a semiconductor gain medium in the laser cavity, and a tuning element for the laser cavity. A phase compensation semiconductor medium is provided in the laser cavity for compensating for dispersion effects over the spectral scan band in some examples.

The swept laser source comprises a tunable pass band filter that restricts the swept laser source to lasing at the discrete selected longitudinal modes. The tuning element comprises a Fabry-Perot tunable filter in the preferred embodiment, which is preferably a MEMS device.

In the typical implementation, the system further comprises an image processing system for controlling the swept laser source and constructing an image from a response of the detector system. A trigger system is used for monitoring the swept laser source and signaling the image processing system to sample the response of the signal/reference detector system.

In general, according to another aspect, the invention features an optical coherence analysis method, which comprises generating an optical signal that is tuned over a spectral scan band at discrete wavelengths. The optical signal is divided between a reference arm leading to a reference reflector and a sample arm leading to a sample. The signals from the reference arm and the sample arm are then optically interfered and detected.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 1 is a schematic block diagram of an optical coherence analysis system to which the invention is applicable;

FIG. 2 is a schematic diagram of a single longitudinal mode hopping tunable laser for the optical coherence analysis system, according to a first embodiment of the present invention;

FIG. 3 is a spectral plot illustrating the relationship between the tunable signal emission from the mode hopping laser, the laser's cavity modes, scan band, and intracavity filter passband;

DETAILED DESCRIPTION OF THE PREFERRED EMBODIMENTS

Figure 4:
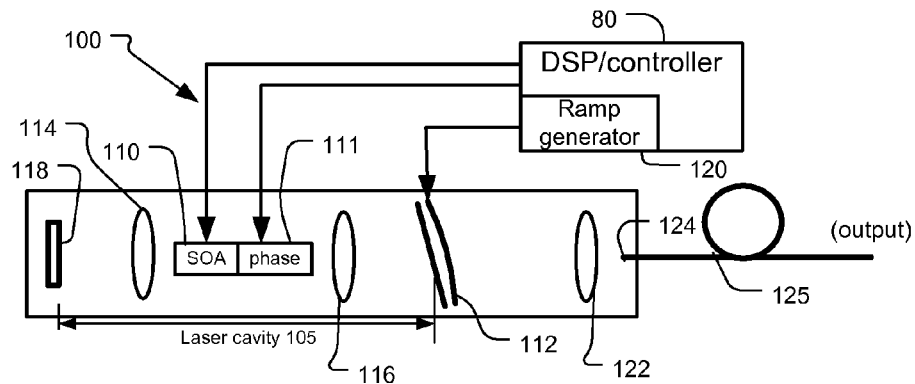
FIG. 4 is a schematic diagram of a single longitudinal mode hopping tunable laser for the optical coherence analysis system with phase compensation, according to a second embodiment of the present invention.

FIG. 1 shows an optical coherence analysis system to which the present invention is applicable.

In more detail, the illustrated system is a time encoded Fourier domain optical coherence tomography system (TEFD-OCT). As such it comprises a tunable narrowband light source. Specifically, a tunable semiconductor diode laser system 100 is used. The light from the tunable laser 100 is output on a fiber 125 to a tap 50. A tap 50 takes a portion of the tunable signal from the tunable laser 100 and directs it to a wavelength or frequency reference system. Specifically, the tap 50 is coupled to a reference filter 52 that applies a known spectral function against the tunable signal. A reference detector 54 detects the tunable signal as it is filtered by the reference filter 52. In one example, the reference filter 52 comprises a fixed etalon providing a series of transmission peaks spaced at known wavelengths.

The light that is not diverted by the tap 50 is provided to a circulator 56. This directs the light from the tunable laser 100 to a coupler 60. The tunable signal is divided by the coupler 60 into a reference arm and a sample arm of the system. Specifically, the optical fiber of the reference arm terminates at the fiber endface 62. The light exiting from the reference arm fiber endface 62 is collimated by a lens 64 and then reflected on a mirror 66 to return back to the coupler 60.

The external mirror 66 has an adjustable fiber to mirror distance. This distance determines the depth range being imaged, i.e. the position in the sample of the zero path length difference between the reference and the sample arms. The distance is adjusted for different sampling catheters and/or imaged samples.

The fiber on the sample arm terminates at the sample arm fiber endface 70. The light exiting from the fiber endface 70 is focused by a lens 72 onto the sample 75. The fiber endface 70 and the lens 72 are controlled by an x-y-z scanner 68. Specifically, the x-y-z scanner 68 scans the focused beam from the fiber endface 70 relative to the sample 75 while collecting the spectral response from the sample 75. The light reflected back into the fiber endface 70 is returned to the coupler 60 which then combines the signals from the reference and sample arms. Light then returns to a first detector 58 via circulator 56 and to a second detector 62.

In examples, the x-y-z scanning is implemented by moving the lens 72 and endface 70 using a three dimensional positioner. In other examples, the x-y-z scanning is implemented by moving the sample 75 relative to the lens 72 and endface 70. In still other examples, the scanning is implemented by rotating and laterally moving the lens 72/endface 70.

The first detector 58 and the second detector 62 function in a balanced detector scheme. Specifically, their electrical responses are combined in a differential amplifier 86 and then sampled in a current embodiment.

In one implementation, an analog to digital converter system 82 of a digital signal processor (DSP) 80 is used to sample the output from the differential amplifier 86.

The analog to digital detection system 82, and usually a second converter, is used to sample the output from the reference detector 54. As a result, the DSP 80 is able to determine the instantaneous wavelength or frequency of the tunable laser 100 as it scans over the scan band.

In one embodiment, the output of the tunable laser is also provided to a direct trigger circuit 75 to provide the sampling trigger to the analog to digital converter system 82. Specifically, the trigger 75 detects the instantaneous amplitude of the tunable laser 100. When the amplitude jumps high as the tunable laser scans and discretely hops between the modes of the laser, the trigger circuit 75 generates a trigger signal that the analog to digital converter system 82 of the digital signal processor 80 uses to trigger and thus sample the output of the differential amplifier 86. In this case such direct laser trigger signal 75 is used instead of the reference detector 54 trigger signal.

Once a complete data set has been collected from the surface of the sample 75 by the operation of the scanner 68 and the spectral response at each one of these points is generated from the tuning of the tunable laser 100, the digital signal processor 80 performs a Fourier transform on the data in order to reconstruct the image and perform a 2D or 3D tomographic reconstruction of the sample 75. This information is generated by the digital signal processor 80 is then displayed on a video monitor 84.

FIG. 2 shows the tunable semiconductor laser 100 according to a first embodiment of the invention.

In more detail, the tunable laser 100 comprises a semiconductor gain chip 110 that is paired with a microelectromechanical (MEMS) angled reflective Fabry-Perot tunable filter 112 to create external cavity tunable laser (ECL).

The semiconductor optical amplifier (SOA) chip 110 is located within a laser cavity 105. In the current embodiment, both facets of the SOA chip are angled and anti-reflection (AR) coated, providing parallel beams from the two facets.

Specifically, each end facet of the SOA 110 has associated lenses 114, 116 that are used to couple the light exiting from either facet of the SOA 110. The first lens 114 couples the light between the back facet of the SOA 110 and a mirror 118. Light exiting out the front facet of the SOA 110 is coupled by a second lens 116 to the reflective Fabry-Perot tunable filter 112.

The angled reflective Fabry-Perot filter is a multi-spatial-mode tunable filter that provides angular dependent reflective spectral response back into the laser cavity 105. This phenomenon is discussed in more detail in incorporated US20060215713A1.

In one specific example, the filter 112 is a curved-flat Fabry-Perot tunable filter that supports multiple spatial modes.

The light transmitted by the tunable filter 112 is coupled through to a third lens 122. This focuses the light down into the endface 124 of an output optical fiber 125, such as single mode fiber, which can also be polarization controlling, such as polarization maintaining (PM), fiber.

The single mode fiber 125 ultimately transports the tunable signal to the coupler 60 and then to each of the reference and sample arms of the optical coherence analysis system 100, see FIG. 1.

In one embodiment, the drive current to the semiconductor optical amplifier 110 is controlled by the digital signal processor 80. Specifically, in one implementation the drive current is controlled to stabilize the power output of the laser 100. Further, in the preferred embodiment, the signal processor 80 either is implemented to function as a ramp generator or a separate ramp generator circuit 120 is provided, which is triggered by the DSP 80. The ramp generator 120 provides a saw-toothed tuning voltage curve to the tunable filter 112 to thereby provide substantially linear frequency tuning with time over the scan band, which also maximizes the tuning performance of the tunable laser 100.

In the preferred embodiment the tunable laser 100 is implemented on an optical bench 107, which is installed in a hermetic package 106. Specifically, this is a micro-optical bench to provide a relatively short laser cavity 105.

FIG. 3 is an exemplary spectral plot illustrating of the relationship between the scan band 310, longitudinal cavity modes 152, the passband 154 for the tunable filter 112, and the laser emission/tunable signal 150.

The scan band 310 for the tunable laser 100 extends over a wavelength range. The passband 154 of the tunable filter 112 is then scanned over the band 310. Its passband is such that it only selects no more than one of the cavity modes 152 of the laser cavity 105. Thus, at points when the passband is directly between cavity modes, spectrally, it is possible that no cavity modes are lasing. However, when the passband 154 aligns with a given cavity mode then the output tunable signal 150 is produced. In this way, the laser system 100 functions as a mode-hopping laser system that only produces an optical signal at the discrete wavelengths of the cavity modes 152.

FIG. 4 shows a second embodiment of the mode hopping tunable laser 100. This includes a second semiconductor chip section 111 that functions as an intra cavity phase or dispersion compensator, which is integral with the semiconductor gain medium in a preferred embodiment. Specifically, there is a certain amount of dispersion during scanning, which implies variation of cavity mode frequency spacing. The cavity 105 is not all air; there is refractive index dispersion in the laser chip, lenses, optical coatings. Also, laser threshold changes over the tuning range. Thus, there will typically be higher carrier density inside the gain chip 110, when it is tuned to the edges of the spectrum. This increased carrier density decreases the chip's refractive index and thereby causes a dispersion-like effect.

The phase compensator 111 controls its refractive index and thus the optical length of the cavity as compensation.

In other embodiments, the compensator includes an electro-optic medium.

In other embodiments, signal processing by the DSP 80 is used to compensate for dispersion in the case of the mode-hopping laser. This involves measuring the laser's tuning dispersion. This dispersion relates to the variation in the optical frequency spacing between modes across the scan band. The collected data is then resampled onto an equally spaced frequency grid before doing the FFT to make the image.

Figure 5:
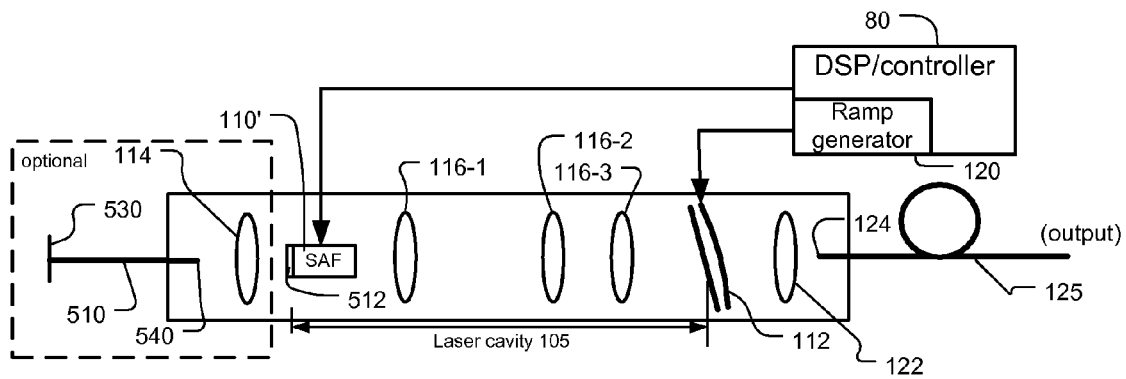
FIG. 5 is a schematic diagram of a single longitudinal mode hopping tunable laser for the optical coherence analysis system using an single angle facet (SAF) semiconductor optical amplifier (SOA) chip, according to a third embodiment of the present invention.

FIG. 5 shows a third embodiment of the mode hopping tunable laser 100. This uses a reflective SOA or single angled facet (SAF) chip 110'. Specifically, the back normal facet 512 of the semiconductor amplifier 110' is reflective to define one end of the laser cavity 105. On the front angled non-reflective facet, a series of three lenses 116-1, 116-2, 116-3 is used to collimate the output of the semiconductor amplifier and relay it to the tunable filter 112, thereby yielding the laser cavity with the desired length. Also in one implementation, light output through fiber 510 is taken, alternatively or in addition to output fiber 125, through the back facet 512 of the reflective optical amplifier SAF 110'. This is used to provide an alternative output of the tunable laser or a second laser output to serve as a possible input to the trigger circuit 75, see FIG. 1.

In a variant design for longer laser cavities, the reflective SOA 110' is replaced with an SOA having antireflection (AR) coated front and rear facets. Further, the facet 540 of the optical fiber 510 is AR coated. This extends the laser cavity 105 into the fiber 510. Thus, with a reflective coated end 530 of the optical fiber, the length of the cavity is made longer to include a portion of the cavity in the fiber 510.

Figure 6:
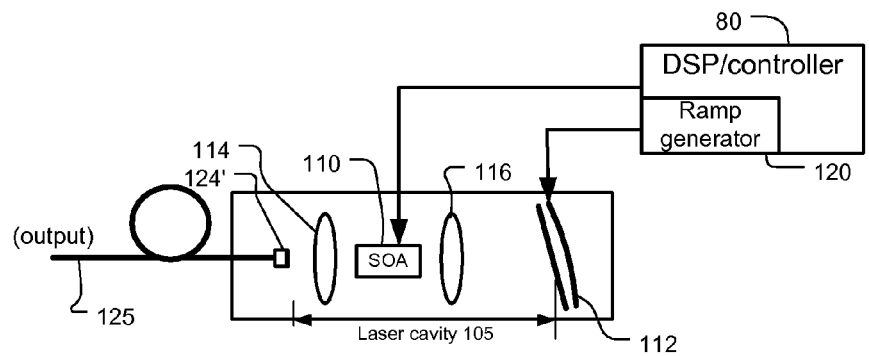
FIG. 6 is a schematic diagram of a single longitudinal mode hopping tunable laser for the optical coherence analysis system taking the tunable optical signal directly from the SOA, according to a fourth embodiment of the present invention.

FIG. 6 shows a fourth embodiment in which the tunable filter 112 forms the one end of the laser cavity 105. The other end of the laser cavity is formed by a mirror 124' formed or deposited on the endface of output optical fiber 125. In preferred embodiment, the mirror is a dielectric multi-layer stack mirror. Further, the fiber 125 preferably has a mode expanded core or an integral mode expander/collimator, such as a fused graded index lens, at the endface/mirror 124' so that the mode size of the fiber output matches the beam size produced by lens 114 from the output of SOA 110.

This embodiment provides higher levels of output power since the output light does not need to pass through the tunable filter 112 and suffer corresponding insertion loss. Also, the beam profile is less distorted, yielding good power coupling. On the other hand, broadband amplified spontaneous emissions from the semiconductor amplifier 110 are not filtered out, as they are when output is taken through the filter 112.

Mode Hopping Laser Specifications

The laser cavity 105 is preferably only about 10-30 millimeters (mm) long, in air. This provides roundtrip times that are on the order 0.07-0.20 nanoseconds (nsec). This short cavity provides for good dynamic laser coherence length upon fast sweep tuning: relatively long coherence length is largely preserved upon fast tuning because of the relatively short cavity.

The passband of the tunable filter 112 is selected to be relatively spectrally narrow in relation to the spectral longitudinal cavity mode spacing of the cavity 105. Specifically, the filter is narrow to ensure only a few, and preferably never more than one, longitudinal mode of the cavity can lase during the scanning of the filter 112. In one example, the passband of the filter 112 is less than 10 giga-Hertz (GHz) wide and is preferably about 5.0 GHz wide, tuning over 100 nanometer scan band near 1300 nm wavelength at 45 kilo-Hertz (kHz) repetition rate. Thus, the filter 112 tunes by one bandwidth in 2.0 nanosecond (nsec). This yields dwell times of 10-57 for 10-30 mm cavities, where dwell time is the number of roundtrips light makes inside laser cavity while the filter tunes by its full width at half maximum. Large dwell times imply static laser coherence length is well preserved under dynamic tuning conditions; for dwell times less than about 2, dynamic laser coherence length decreases rapidly.

First single-mode laser:
Filter 112, bandwidth 6-8 GHz.
Length of laser cavity 105: ~17.5 mm, Mode Spacing ~8.6 GHz.
Lorentzian filter transmission at side-mode: 0.11-0.20.
Good single mode operation with low, >30 dB, sidemodes.

Second single-mode laser:
Filter 112 bandwidth: 9-12 GHz.
Length of laser cavity 105: 21 mm, Mode Spacing ~7.0 GHz.
Lorentzian filter transmission at side-mode: 0.29-0.42.
side-mode suppression ration (SMSR) only ~10-15 dB.

Figure 7:
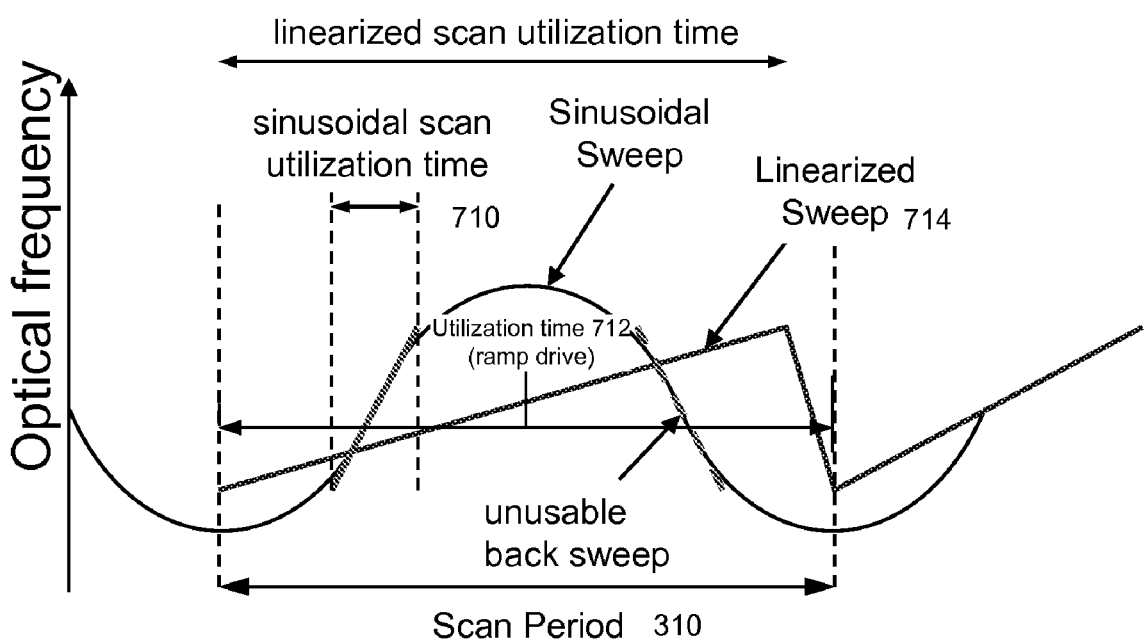
FIG. 7 is a plot of optical frequency as a function of scan period showing the inventive saw-toothed tuning ramp compared with a convention sinusoid tuning drive.

FIG. 7 shows the conventional sinusoidal filter tuning drive. As a result, only a small portion of the total scan period has a near linear tuning curve (see sinusoid scan utilization time period 710). This sinusoidal drive signal is necessitated by the relative high mass spectral tuning elements used in convention ECL devices, which requires driving such tunable filters sinusoidally in time near their resonant frequency. MEMS tunable filters, preferably used in the inventive lasers, have high resonance frequencies and their frequency tuning with time can be linearized for repetition frequencies of 50-100 kHz and higher.

According to the present invention, the ramp generator 120 produces a sawtoothed drive signal 714 to provide a linearized sweep that extends over 50% and preferably greater than 80% of the scan period 310, providing much higher duty cycles of 50-80% and greater.

Figure 8:
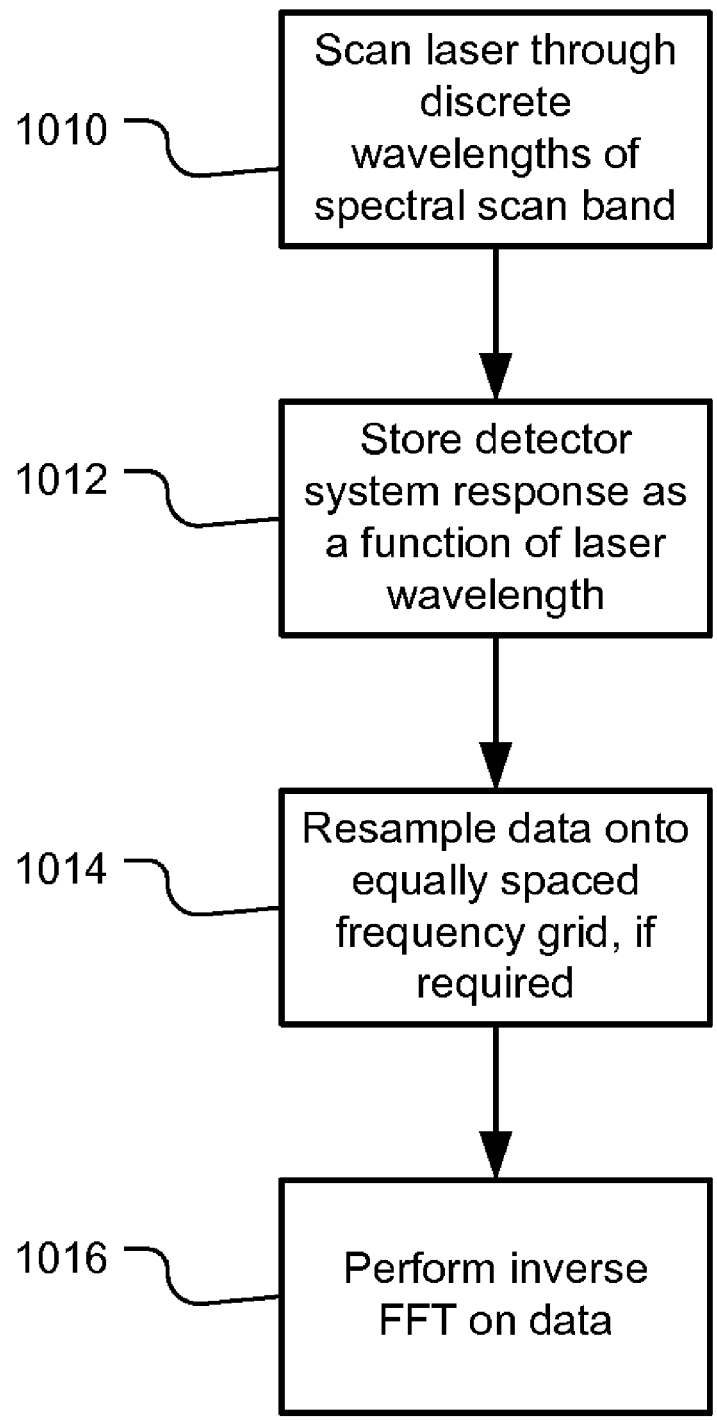
FIG. 8 is a flow diagram illustrating process for optical coherence analysis.

FIG. 8 illustrates the process performed by the optical coherence analysis system. Specifically, in step 1010 the laser is scanned through the discrete wavelengths of the spectral scan band. In step 1012, the detector system response is stored as a function of wavelength by the digital signal processor 80 in one example. The data are then reassembled on to an equally spaced frequency grid in step 114. This is required if the discrete laser scan frequencies do not have the same spectral separation.

Finally, in step 1016 an inverse Fourier transform is applied to the data in order to reconstruct the image of the sample.

While this invention has been particularly shown and described with references to preferred embodiments thereof, it will be understood by those skilled in the art that various changes in form and details may be made therein without departing from the scope of the invention encompassed by the appended claims.

What is claimed is:

1. An optical coherence analysis system comprising:
   a swept laser source that generates an optical signal that is tuned over a spectral scan band, the laser emitting one wavelength mode at a time and tuning discretely over wavelengths associated with longitudinal modes of the swept laser source;
   a beam splitter for dividing the optical signal between a reference arm leading to a reference reflector and a sample arm leading to a sample; and
   a detector system for detecting the optical signal from the reference arm and the sample arm.

2. An optical coherence analysis system as claimed in claim 1, wherein the swept laser source comprises:
   a laser cavity having at least two reflectors, which define the longitudinal cavity modes;
   a semiconductor gain medium in the laser cavity; and
   a tuning element for the laser cavity.

3. An optical coherence analysis system as claimed in claim 2, wherein the tuning element provides a tunable pass band that restricts the swept laser source to lasing at the single discrete ones of the longitudinal modes.

4. An optical coherence analysis system as claimed in claim 3, wherein the tuning element comprises a Fabry-Perot tunable filter.

5. An optical coherence analysis system as claimed in claim 3, wherein the tuning element comprises an angled reflective Fabry-Perot tunable filter.

6. An optical coherence analysis system as claimed in claim 3, wherein the tuning element comprises a MEMS Fabry-Perot tunable filter.

7. An optical coherence analysis system as claimed in claim 3, wherein the tuning element comprises a MEMS angled reflective Fabry-Perot tunable filter.

8. An optical coherence analysis system as claimed in claim 2, further comprising a phase compensation medium in the laser cavity for compensating for dispersion effects over the spectral scan band.

9. An optical coherence analysis system as claimed in claim 8, wherein phase compensation medium is semiconductor medium.

10. An optical coherence analysis system as claimed in claim 8, wherein phase compensation medium is an electro-optic medium.

11. An optical coherence analysis system as claimed in claim 8, wherein phase compensation semiconductor medium is integral with the semiconductor gain medium.

12. An optical coherence analysis system as claimed in claim 2, wherein one of the reflectors is integral with the semiconductor gain medium.

13. An optical coherence analysis system as claimed in claim 2, wherein one of the reflectors is integral with tuning element.

14. An optical coherence analysis system as claimed in claim 2, wherein a bandwidth of the tuning element and spacing between the longitudinal modes enables only individual ones of the longitudinal modes to lase as the optical signal is tuned over the spectral scan band.

15. An optical coherence analysis system as claimed in claim 2, wherein the optical signal is taken from the laser cavity through the tuning element.

16. An optical coherence analysis system as claimed in claim 2, wherein the optical signal is taken from the laser cavity through the semiconductor gain medium.

17. An optical coherence analysis system as claimed in claim 1, wherein longitudinal mode spacing of the longitudinal modes is greater than 4 GHz.

18. An optical coherence analysis system as claimed in claim 1, wherein longitudinal mode spacing of the longitudinal modes is between 5 GHz and 15 GHz.

19. An optical coherence analysis system as claimed in claim 1, wherein a coherence length of the optical signal is greater than 10 mm at a tuning rate of greater than 25 kHz.

20. An optical coherence analysis system as claimed in claim 1, further comprising:
    an image processing system for controlling the swept laser source and constructing an image from a response of the detector system; and
    a trigger system for monitoring a magnitude of the optical signal detected by the detector system and signaling the image processing system to sample the response of the detector system.

21. An optical coherence analysis system as claimed in claim 1, further comprising an image processing system for resampling data from the detector system for the discrete wavelengths to equally spaced optical frequencies.

22. An optical coherence analysis system as claimed in claim 1, wherein the beam splitter is a fiber coupler.

23. An optical coherence analysis system as claimed in claim 1, wherein the beam splitter combines the optical signal from the reference arm and optical signal from the signal arm prior to detection by the detector system.

24. An optical coherence analysis method comprising generating an optical signal that is tuned over a spectral scan band at discrete wavelengths by generating the discrete wavelengths at longitudinal modes of a laser cavity comprising a semiconductor gain medium and a tuning element for the laser cavity that restricts lasing of the laser cavity to only discrete ones of the longitudinal modes;
    dividing the optical signal between a reference arm leading to a reference reflector and a sample arm leading to a sample; and
    detecting the optical signal from the reference arm and the sample arm.

25. An optical coherence analysis method as claimed in claim 24, further compensating for dispersion effects over the spectral scan band.

26. An optical coherence analysis method as claimed in claim 24, wherein the tuning element comprises a Fabry-Perot tunable filter.

27. An optical coherence analysis method as claimed in claim 24, wherein the tuning element comprises a MEMS Fabry-Perot tunable filter.

28. An optical coherence analysis method as claimed in claim 24, further comprising configuring a bandwidth of the tuning element and spacing between longitudinal modes to enable only individual ones of the longitudinal modes to lase as the optical signal is tuned over the spectral scan band.

29. An optical coherence analysis method as claimed in claim 24, further comprising taking the optical signal from the laser cavity through the tuning element.

30. An optical coherence analysis method as claimed in claim 24, further comprising taking the optical signal from the laser cavity through the semiconductor gain medium.

31. An optical coherence analysis method as claimed in claim 24, wherein longitudinal mode spacing is greater than 4 GHz.

32. An optical coherence analysis method as claimed in claim 24, wherein longitudinal mode spacing is between 5 GHz and 15 GHz.

33. An optical coherence analysis method as claimed in claim 24, wherein a coherence length of the optical signal is greater than 10 mm at a tuning rate of greater than 25 kHz.

34. An optical coherence analysis method as claimed in claim 24, further comprising:
    controlling the tuning of the optical signal and constructing an image from a detection of the optical signal; and
    monitoring a magnitude of the optical signal and controlling sampling of the optical signal in response to the monitored magnitude.

35. An optical coherence analysis method as claimed in claim 24, further comprising resampling data from detection of the optical signal for the discrete wavelengths to equally spaced optical frequencies.

* * * * *